United States Patent [19]

Jerusik et al.

[11] Patent Number: 5,004,749
[45] Date of Patent: Apr. 2, 1991

[54] CONCENTRATED AQUEOUS SOLUTION OF GLUTARALDEHYDE AND 1,2-BENZISOTHIAZOLIN-3-ONE

[75] Inventors: Russell J. Jerusik, Wilmington, Del.; Paul F. Mahon, Oldham, England

[73] Assignees: Imperial Chemical Industries plc, London, England; ICI Americas Inc., Wilmington, Del.

[21] Appl. No.: 340,935

[22] Filed: Apr. 20, 1989

[51] Int. Cl.$^5$ .............................................. A10N 43/80
[52] U.S. Cl. ..................................... 514/372; 514/949
[58] Field of Search ................ 514/372, 373, 327, 949

[56] References Cited

FOREIGN PATENT DOCUMENTS 234860  4/1985  Japan .................................... 514/372

OTHER PUBLICATIONS

K-E Rasmussen et al., "Glutaraldehye, the Influence of pH, Temperature and Buffering on Polymerization Rate", Histochemistry, vol. 38, pp. 19–26 (1974).

*Primary Examiner*—Stanley J. Friedman
*Assistant Examiner*—Kevin Weddington
*Attorney, Agent, or Firm*—William E. Dickheiser

[57] ABSTRACT

Concentrated aqueous solutions of 1,2-benzisothiazolin-3-one are prepared by incorporating a buffering agent such that the pH of the solution is between about 3.0 and 7.0, and further adding a sufficient amount of glutaraldehyde such that a greater amount of such 1,2-benzisothiazolin-3-one is in solution than would be in solution if such glutaraldehyde were not present. Also disclosed is a synergistic biocidal composition comprising glutaraldehyde and 1,2-benzisothiazolin-3-one, as well as an aqueous-based industrial composition comprising such synergistic biocidal composition.

14 Claims, No Drawings

CONCENTRATED AQUEOUS SOLUTION OF GLUTARALDEHYDE AND 1,2-BENZISOTHIAZOLIN-3-ONE

FIELD OF THE INVENTION

The present invention is directed to an aqueous composition comprising 1,2-benzisothiazolin-3-one in water, which composition further comprises a buffering agent such that the pH of the composition is between about 3.0 and 7.0, and a sufficient amount of glutaraldehyde such that a greater amount of such 1,2-benzisothiazolin-3-one is in solution than would be present in solution if such glutaraldehyde were not present. This composition, which exhibits desirable storage stability, may be diluted and employed as a biocidal composition which exhibits synergistic activity.

BACKGROUND OF THE INVENTION

Glutaraldehyde and 1,2-benzisothiazolin-3-one are both individually known to exhibit desirable biocidal activity. Thus, Payne et al (U.S. Pat. No. 4,188,376) discloses that 1,2-benzisothiazolin-3-one is known to be a very effective biocide, particularly for the protection of aqueous media against infection by microorganisms. Similarly Clifford et al (U.S. Pat. No. 4,539,071) exemplify the biocidal efficacy of glutaraldehyde alone.

While the blending of glutaraldehyde with other biocides, such as 2-methyl-4-isothiazolin-3-one and 5-chloro-2-methyl-4-isthiazolin-3-one has been accomplished with desirable results in the past (see, e.g., U.S. Pat. No. 4,539,071 to Clifford et al), similar results have not been exemplified for blends of glutaraldehyde with 1,2-benzisothiazolin-3-one. It is believed that this stems in large part from the perceived incompatibility of glutaraldehyde with 1,2-benzisothiazolin-3-one.

Thus, it is well accepted that glutaraldehyde should be formulated into acidic compositions, as this compound polymerizes rapidly in alkaline environments See, e.g., K.-E. Rasmunen et al, "Glutaraldehyde. The Influence of pH, Temperature and Buffering on the Polymerization Rate", Histochemistry, Vol. 38, pp. 19-26 (1979): S. Thomas et al, "Temperature-Induced Changes in the Sporicidal Activity and Chemical Properties of Glutaraldehyde", Applied Microbiology, Vol. 28, No. 3, pp. 331-335 (September, 1974). While Japanese Patent Publication 63-112532 does disclose weakly alkaline aqueous glutaraldehyde solutions, such result is only achieved at the expense of biocidal activity.

Conversely, due to the low solubility of 1,2-benzisothiazolin-3-one in water under acidic conditions, it has become well accepted that this compound must be formulated under alkaline conditions to produce concentrated aqueous solutions. Thus, for example, U.K. Patents Numbers 1,171,253 and 1,330,531 both show aqueous formulations of 1,2-benzisothiazolin-3-one which are stabilized by the addition of an appropriate amine or mixture of amines Consequently, it is completely unexpected that a concentrated aqueous solution of 1,2-benzisothiazolin-3-one and glutaraldehyde could be prepared, much less that such combination, when diluted by adding it to an aqueous-based industrial product, would exhibit synergistic biocidal activity.

DESCRIPTION OF THE INVENTION

In one aspect, this invention is directed to a concentrated aqueous composition comprising 1,2-benzisothiazolin-3-one and water, which composition further comprises a buffering agent such that the pH of the composition is between about 3.0 and 7.0, and a sufficient amount of glutaraldehyde such that a greater amount of such 1,2-benzisothiazolin-3-one is in solution than would be present in solution if such glutaraldehyde were not present.

In other aspects, this invention is directed to a synergistic biocidal composition comprising glutaraldehyde and 1,2-benzisothiazolin-3-one as well as to an aqueous-based industrial product comprising an effective amount of such a synergistic composition.

The concentrated aqueous composition of this invention comprises four components—i.e., glutaraldehyde, 1,2-benzisothiazolin-3-one, water and a buffering agent.

As is employed herein, the term "buffering agent" refers to any compound and/or combination of compounds which will maintain the pH of the composition at between about 3.0 and 7.0, preferably at between about 3.2 and about 6.8, most preferably between about 3.2 and about 4.8; and which will not adversely interfere with the biocidal activity of the composition.

Such buffering compositions are well known to those skilled in the art, and will typically comprise a partially neutralized blend of an acid and an appropriate base, although substances which contain basic and acidic groups which can combine with added base or acid may also be employed. Illustrative of such buffering agents include the combination of a weak acid, such as acetic, formic, chloroacetic or propionic acid or the like, with an appropriate base such as sodium hydroxide, sodium acetate or the like. A particularly preferred buffering agent for use in the concentrated composition of this invention comprises acetic acid and sodium acetate. The relative amounts of each component in such buffering agents may be readily calculated by one of ordinary skill in the art from buffer tables such as those present in the "CRC Handbook of Chemistry and Physics", CRC Press, Inc. pp. D-144 et seq., 66th Ed. (1985-86).

The concentrated aqueous compositions of this invention may be formed by mixing the components in any order under agitation. Typically, however, an appropriate amount of 1,2-benzisothiazolin-3-one is added to a solution of glutaraldehyde under agitation. The buffering agent is then added while the agitation continues. Such agitation may be accomplished by any means well known to one of ordinary skill in the art, including mechanical stirrers, magnetic stirrers, ultrasonic agitation means, and the like. In circumstances where a more concentrated solution of 1,2-benzisothiazolin-3-one is desired, it is preferred that an excess of such compound be added to an appropriately buffered aqueous glutaraldehyde solution, and the mixture filtered to remove undissolved 1,2-benzisothiazolin-3-one and insoluble impurities.

Preferably the weight ratio of glutaraldehyde to 1,2-benzisothiazolin-3-one employed in the compositions of this invention may range between about 50:1 and about 5:1, and will more preferably be between about 20:1 and about 10:1, most preferably between about 15:1 and about 13:1. Preferably, the weight ratio of active material (i.e. glutaraldehyde plus 1,2-benzisothiazolin-3-one) to water will range between about 1.0:1 and about 1.2:1, although lower or higher ratios may be employed, so long as more 1,2-benzisothiazolin-3-one is in solution than would be in solution if no glutaraldehyde were present.

The amount of buffering agent which should be employed for any particular concentrated composition may be readily determined by one of ordinary skill in the art. It should be noted that, although concentrated solutions of glutaraldehyde typically possess a pH between about 3.0 and 7.0, a buffering agent is necessary in the 1,2-benzisothiazolin-3-one/glutaraldehyde blends to avoid pH drift which would adversely affect the storage stability of such compositions, especially at extreme temperatures.

The concentrated aqueous compositions of this invention are typically employed as biocidal agents in aqueous-based industrial products by adding them to such products in appropriate amounts such that a biocidally effective amount of active material is present in such industrial products. Illustrative of the industrial products in which such combinations may be employed are calcium carbonate slurries, kaolin slurries, tape joint compounds, and latices. The compositions of such aqueous-based industrial compositions are well known to those of skill in the art. These concentrated compositions exhibit admirable long term stability as well as desirable temperature resistance.

An unexpected benefit which has been recognized in conjunction with the invention of the concentrated solutions described above, is that synergistic biocidal activity is achieved when 1,2-benzisothiazolin-3-one is employed together with glutaraldehyde. Because such synergy is observed even at concentrations of active material well below those of the concentrated liquid compositions described above, it is to be noted that such synergy will be present even in non-concentrated formulations of glutaraldehyde with 1,2-benzisothiazolin-3-one wherein no buffering agent is present. Accordingly, in another aspect, this invention is directed to a synergistic biocidal composition comprised of 1,2-benzisothiazolin-3-one and glutaraldehyde.

Preferably the weight ratios of glutaraldehyde to 1,2-benzisothiazolin-3-one employed in such synergistic compositions may range from about 17:1 to about 12.5:1, more preferably from about 15:1 to about 13:1. The control exhibited by such combinations is greater than that which would have been expected were mere additive results involved.

Such synergistic compositions are employed in synergistic amounts—i.e., amounts in which less than complete control would be expected for either of the components used alone, or both components if only additive control were expected. Such compositions may be usefully employed in the industrial products described above.

EXAMPLES

The following Examples are intended to further illustrate the present invention and are not intended to limit the scope of the invention in any manner whatsoever.

EXAMPLE 1

Several solutions of deionized water and a buffering agent were prepared possessing pH's of 3.2, 4.8 and 6.8 respectively Specifically 0.2 M acetic acid and 0.2 M sodium acetate were utilized. A pH 3.2 solution was attained by adding 12.5 ml of 0.2 M acetic acid to 100 ml of deionized water. The pH 4.8 solution was prepared by adding 22.5 ml of 0.2 M acetic acid plus 27.5 ml of 0.2 M sodium acetate brought to a total volume of 100 ml with deionized water. Finally the pH of 6.8 solution was created by adding 4.1 ml of 0.2 M sodium acetate plus 1 drop of 0.2 M acetic acid to 100 ml of deionized water. The solubility of 1,2-benzisothiazolin-3-one ("BIT") in the form of Proxel ® Press Paste comprising 73% BIT as an industrial grade wet powder (available from Imperial Chemical Industries PLC), in each solution at 25° C. was determined by adding known quantities of BIT while agitating such solutions, filtering off the undissolved BIT, and any insoluble impurities then weighing the filtrate to determine how much BIT was in solution. Employing the same buffering agents, solutions with 50% aqueous glutaraldehyde were prepared having pH's of 3.2, 4.8 and 6.8 respectively. A twenty ml solution having a pH of 3.2 was attained with 1.45 ml of acetic acid; the twenty ml solution having a pH of 4.8 contained acetic acid and sodium acetate in a 3:1 weight ratio and the twenty ml solution having a pH of 6.8 contained 1.25 g of sodium acetate. The solubility of BIT in each solution was determined as described above. The results of such tests, presented in grams of BIT soluble per 100 grams of solvent, are summarized in Table 1 below.

TABLE I

| Solubility of BIT (in grams/100 grams solvent) | | | |
|---|---|---|---|
| SOLVENT | pH 3.2 | pH 4.8 | pH 6.8 |
| Deionized Water | 0.32 | 0.11 | 0.04 |
| 50% Aqueous Glutaraldehyde | 3.18 | 3.38 | 3.04 |

The above results indicate that the solubility of 1,2-benzisothiazolin-3-one is increased considerably by the addition of glutaraldehyde under the above conditions.

EXAMPLE 2

In order to compare the composition of the present invention with that disclosed in U.S. Pat. No. 4,539,071 (Clifford et al) a stable aqueous composition of isothiazolone, the following experiment was performed. To deionized water were added 0.2 percent cupric nitrate, 9 percent magnesium chloride and 15 percent magnesium nitrate, all in percent by weight. The solubility of 1,2-benzisothiazolin-3-one in such solution was found to be essentially nil, thereby showing that such prior art method for providing stable aqueous solutions of isothizaolones is ineffective for producing a stable aqueous solution of 1,2-benzisothiazolin-3-one.

EXAMPLE 3

Several forty gram samples of a calcium carbonate slurry (Gamma-Fil 90, available from the Georgia Marble Company) which were free of microbial growth, were prepared. These samples were divided into four groups. The first group was dosed with varying amounts of glutaraldehyde (in the form of a 50 percent aqueous solution); the second group was dosed with varying amounts of 1,2-benzisothiazolin-3-one the third group was dosed with varying amounts of glutaraldehyde (in the form of a 50 percent aqueous solution) and of 1,2-benzisothiazolin-3-one (in the form of Proxel ® Press Paste) in a 14:1 ratio by weight of glutaraldehyde:BIT a fourth group was left untreated as a control. These samples were each inoculated three times on a weekly basis with an inoculum which contained the following microorganisms: *Acinetobacter calcoaceticus, Pseudomonas aeruginosa, Enterobacter cloacae* and *Escherichia coli.* The minimum inhibitory concentration (MIC) values were determined for preservative levels effective in reducing the contaminating microorganisms to less than ten colony forming units/ml for the first three groups. The number of colony forming units/ml in the control group was also determined. The results of such evaluation are summarized in TABLE II below.

TABLE II

MIC values (in parts per million of Active Ingredient) Calcium Carbonate Slurry

|  | Week 1 | Week 2 | Week 3 |
|---|---|---|---|
| Glutaraldehyde | 250 | 500 | 500 |
| BIT | 285 | >570 | 380 |
| BIT + Glutaraldehyde (1:14) | 265 | 265 | 265 |
| Control | $3.3 \times 10^6$ | $9.2 \times 10^6$ | $1.8 \times 10^7$ |

EXAMPLE 4

A sample of kaolin slurry with significant microbial spoilage was dosed with a range of concentrations of 1,2-benzisothiazolin-3-one, glutaraldehyde, and 1,2-benzisothiazolin-3-one plus glutaraldehyde (1:14 weight ratio). A sample was included, antimicrobial free, for control purposes with determinations of the colony forming units/ml. MIC values (in parts per million of Active Ingredient) to reduce microbial contamination to less than ten colony forming units/ml were determined by the absence of detectable growth by dilution plate counts. The results of such testing are summarized in Table III.

TABLE III

MIC Values (ppm) Kaolin Slurry

| | Time (Days) | | | |
|---|---|---|---|---|
| | 1 | 2 | 3 | 7 |
| Glutaraldehyde | 250 | 150 | 200 | 250 |
| BIT | 178 | >178 | >178 | 133 |
| BIT + Glutaraldehyde (1:14) | 217 | 107 | 160 | 160 |
| Control | $3.2 \times 10^7$ | $2.9 \times 10^7$ | $5.8 \times 10^7$ | $1.0 \times 10^7$ |

The results for Examples 3 and 4 were quantified with respect to the synergy shown through the application of an equation described in Berenbaum, M.C. "A method for Testing for Synergy with Any Number of Agents" The Journal of Infectious Diseases, Vol 137, No. 2 pp 122-130 (February, 1978). The relevant equation is as follows:

$$\frac{Ac}{Ae} + \frac{Bc}{Be} = Z$$

Wherein:

Ac = First antimicrobial active ingredient, effective level in the combination.

Ae = First antimicrobial active ingredient, effective independent activity level.

Bc = Second antimicrobial agent ingredient, effective level in the combination.

Be = Second antimicrobial active ingredient, effective independent activity level.

If Z is less than 1, synergy is present. If Z equals 1, additive interaction is present. If Z is greater than 1, an antagonistic interaction is present. The results of such quantification are presented in TABLE IV.

TABLE IV

| Substrate | Synergy Equation Values | | |
|---|---|---|---|
| | Weeks | | |
| | 1 | 2 | 3 |
| Calcium Carbonate Slurry (Example 3) | 1.06 | 0.53* | 0.55 |
| | Days | | | |
| | 1 | 2 | 3 | 7 |
| Kaolin Slurry (Example 4) | 0.88 | 0.74* | 0.81* | 0.68 |

*BIT values utilized as noted in TABLES II and III even though actual MIC's are higher, where a greater than symbol (>) is present.

The calcium carbonate slurry example shows that while glutaraldehyde undergoes a reduction in antimicrobial activity during the second and third challenges with microbial insults the combination maintains its antimicrobial potency with resulting synergy. While the results for week 1 indicate that some slight antagonism may be observed, it is believed that this result is within experimental error and biological variability such that no actual antagonism is in fact present.

The kaolin slurry example indicates consistent synergistic interactions, between BIT and glutaraldehyde.

Therefore, the above results for Examples 3 and 4 illustrate the unexpected synergistic biocidal activity exhibited by the combination of 1,2-benzisothiazolin-3-one and glutaraldehyde in aqueous-based industrial compositions.

What is claimed is:

1. A composition comprising 1,2-benzisothiazolin-3-one and water, which composition further comprises a buffering agent such that the pH of the composition is between about 3.0 and 7.0, and a sufficient amount of glutaraldehyde such that a greater amount of such 1,2-benzisothiazolin-3-one is in solution than would be present in solution if such glutaraldehyde were not present.

2. A composition in accordance with claim 1 wherein the pH of the composition is between about 3.2 and about 6.8.

3. A composition in accordance with claim 2 wherein the pH of the composition is between about 3.2 and about 4.8.

4. A composition in accordance with claim 1 wherein said buffering agent comprises acetic acid and sodium acetate.

5. A composition in accordance with claim 1 wherein the weight ratio of glutaraldehyde to 1,2-benzisothiazolin-3-one is between about 50:1 and about 5:1.

6. A composition in accordance with claim 5 wherein the weight ratio of glutaraldehyde to 1,2-benzisothiazolin-3-one is between about 20:1 and about 10:1.

7. A composition in accordance with claim 6 wherein the weight ratio of glutaraldehyde to 1,2-benzisothiazolin-3-one is between about 15:1 and about 13:1.

8. A method of protecting aqueous-based industrial products from biological contamination comprising adding a synergistically effective amount of a synergistic biocidal composition comprising glutaraldehyde and 1,2-benzisothiazolin-3-one
wherein the weight ratio is between about 50:1 and about 5:1.

9. A method in accordance with claim 8 wherein the weight ratio of glutaraldehyde to 1,2-benzisothiazolin-3-one is between about 17:1 and about 12.5:1.

10. A method in accordance with claim 9 wherein the weight ratio of glutaraldehyde to 1,2-benzisothiazolin-3-one is between about 15:1 and about 13:1.

11. A method in accordance with claim 8 wherein said aqueous-based industrial product is a calcium carbonate slurry.

12. A method in accordance with claim 8 wherein said aqueous-based industrial product is a kaolin slurry.

13. A method in accordance with claim 8 wherein said aqueous-based industrial product is a tape joint compound.

14. A method in accordance with claim 8 wherein said aqueous-based industrial product is a latex.

* * * * *